United States Patent [19]

Schulze

[11] 4,154,724

[45] May 15, 1979

[54] POLYETHER POLYUREIDES AND RESINOUS COMPOSITIONS THEREFROM

[75] Inventor: Heinz Schulze, Austin, Tex.

[73] Assignee: Texaco Development Corp., White Plains, N.Y.

[21] Appl. No.: 700,640

[22] Filed: Jun. 28, 1976

[51] Int. Cl.² .................... C08G 71/02; C08G 18/64; C07C 127/00; C07C 157/02

[52] U.S. Cl. .................. 528/68; 260/552 R; 260/553 R; 528/76; 528/363; 528/367

[58] Field of Search ................ 260/77.5 CH, 77.5 C, 260/552 R, 553 R, 553 CD, 555 R

[56] References Cited

U.S. PATENT DOCUMENTS

| | | | |
|---|---|---|---|
| 3,080,343 | 3/1963 | Ham | 260/77.5 C |
| 3,704,321 | 11/1972 | Kmet et al. | 260/552 R |
| 3,996,269 | 12/1976 | Markiewicz | 260/482 C |
| 4,002,598 | 1/1977 | Waddill et al. | 260/553 R |

FOREIGN PATENT DOCUMENTS

| | | | |
|---|---|---|---|
| 647644 | 8/1962 | Canada | 260/77.5 C |
| 717151 | 8/1965 | Canada | 260/77.5 C |
| 981813 | 1/1965 | United Kingdom | 260/77.5 C |
| 1104209 | 2/1968 | United Kingdom | 260/77.5 CH |

*Primary Examiner*—H. S. Cockeram
*Attorney, Agent, or Firm*—Carl G. Ries; Thomas H. Whaley; Kenneth R. Priem

[57] ABSTRACT

Novel polyether polyureides useful in the manufacture of plastics, sealants, molds, foams and coatings. The novel composition comprises a ureido-terminated polyoxyalkylene prepared by reacting a primary amine-terminated polyoxyalkylene with urea at temperatures in the range from about 120° C. to about 150° C. in a molar ratio of about one mole of urea for each terminal primary amino group.

25 Claims, No Drawings

POLYETHER POLYUREIDES AND RESINOUS COMPOSITIONS THEREFROM

BACKGROUND OF THE INVENTION

1. Field of the Invention

This invention generally pertains to ureido-terminated compounds and more particularly to ureido-terminated polyoxyalkylene compounds and their method of preparation.

2. Prior Art

Ureido-terminated compounds are generally well known in the art. These compounds have many well known uses. Among the most widely known is the polymeric condensation with an aldehyde to form urea-aldehyde resins.

Aliphatic or aromatic, compounds having a single terminal ureido group are well known. It has been disclosed in U.S. Pat. No. 2,145,242 to Arnold that di-ureido terminated alihatic compounds can be produced by reacting an aliphatic diamine wherein each terminal amine has at least one labile hydrogen with urea.

Additionally, polyalkylenepolyamine-containing compounds having primary or secondary amine termination are shown to form ureido containing compounds. For example, triethylenetetramine can be reacted with urea at temperatures of 120° C. to 160° C. to form thermoplastic resinous polymers soluble in alcohols, ketones, and esters but insoluble in hydrocarbons and only limitedly soluble in water.

Further, it has been disclosed that aliphatic primary diamines and particularly those wherein the amine groups are separated by alkylene hydrocarbons yield crystalline monomeric compounds when reacted with urea. These compounds have a relatively high melting point, i.e., 180° C.–190° C. and are relatively insoluble in even boiling alcohol. Additionally, Arnold discloses that mono oxycontaining amines yield ureas which are similar in characteristic.

It has now been discovered that a certain class of polyether primary amine terminated compounds form polyether containing polyureides. These compounds unexpectedly form homogeneous solutions with aqueous formaldehyde and solvents. Additionally, the compounds of the instant invention reduce the punking of phenolic foams while simultaneously forming a portion of the polymer.

SUMMARY OF THE INVENTION

According to the broad aspects of the instant invention, a polyether polyureide comprises a ureido-terminated polyoxyalkylene material. The novel polyether polyureido compounds are formed by the reaction of a ureido group forming compound with a polyoxyalkylenepolyamine of the formula $$[H_2N(CHCHO)_n]_r Z$$
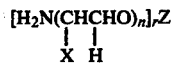

wherein X is a hydrogen, a methyl radical or an ethyl radical; Z is a hydrocarbon radical having from 2 to 5 carbon atoms forming from 2 to 4 external ether linkages; n is a number from 1 to about 20 and r is a number from 2 to 4.

DESCRIPTION OF THE PREFERRED EMBODIMENT

According to a preferred embodiment, a polyether polyureide is prepared by admixing and reacting a polyoxyalkylenediamine or triamine having a molecular weight from about 400 to 2,000 with urea at temperatures of from about 130° to 140° C. until ammonia gas development ceases and stripping the crude reaction product at about 100° C. to 110° C. in vacuum to recover the product.

The novel polyether polyureides in accordance with the instant invention are those compounds containing a polyoxyalkylene radical and terminal ureido groups of the formula

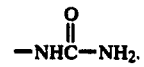
$$-NHC-NH_2.$$

The polyoxyalkylene polyamines useful in forming the polyether polyureides of the instant invention may be depicted by the formula:

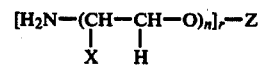
$$[H_2N-(CH-CH-O)_n]_r-Z$$
$$\quad\quad\quad X\quad H$$

wherein X is hydrogen, a methyl radical or an ethyl radical; Z is a hydrocarbon radical having from 2 to 5 carbon atoms forming from 2 to 4 external ether linkages; n is a number from 1 to about 20 and r is a number from 2 to 4. The most preferred polyoxyalkylenepolyamines are the polyoxypropylenediamines wherein X is a methyl radical, n is a number from 2 to 17, Z is a 1,2-propylene radical and r is about 2 or 3. These polyoxyalkylenepolyamines can be prepared by known methods as disclosed in U.S. Pat. No. 3,236,895 and U.S. Pat. No. 3,654,370.

Generally, the polyether ureides of the instant invention are formed by the reaction of the polyoxyalkylenepolyamine with a ureido forming compound. The most preferred ureido forming compound is urea. When urea is employed as a reactant, the reaction proceeds with the evolution of ammonia and the terminal primary amino groups of the polyoxyalkylenepolyamine are converted directly to ureido groups.

While urea is the preferred ureido forming compound, other ureido forming compounds can be utilized within the scope of the invention. Since the polyoxyalkylenepolyamine reactant already contains terminal primary amino groups, compounds which supply the

$$\overset{O}{\underset{\|}{C}}-NH_2$$

radical can be utilized. Examples of such compounds are the isocyanates of the general formula M+NCO− wherein M+ is generally an alkali metal such as potassium, sodium and the like. The preferred isocyanates that can be used in accordance with the instant invention are sodium and potassium isocyanate primarily because of availability.

The functionality of the polyoxyalkylenepolyamine is dependent upon the number of terminal primary amino groups. It will be realized that each mole of ureido forming compound reacts with a single terminal primary amino group of the polyoxyalkylenepolyamine. It is particularly important that in forming the compounds of the instant invention a specific molar ratio of reactants be maintained. Specifically, about 1 mole of ureido forming compound for each amino group of the polyoxyalkylenepolyamine is required. Thus, for example, with a diamine about 2 moles of ureido forming compound is utilized. Preferably the instant reaction is carried out in the presence of a slight excess of ureido forming compound to assure complete conversion of the amino groups. It will be realized that a larger access of ureido forming compound may be desirable for certain applications, i.e., formation of urea-aldehyde resins.

The polyether ureido terminated compounds of the instant invention can be simply described as polyoxyalkylene containing compounds having terminal ureido groups. In accordance with the greatly preferred embodiment, the ureido terminated compounds are of the formula:

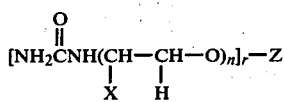

wherein X is hydrogen, a methyl radical or an ethyl radical; Z is a hydrocarbon radical having 2 to 5 carbon atoms forming from 2 to 4 external ether linkages; n is a number from 1 to about 20; and, r is a number from 2 to 4. The most preferred polyoxyalkylenepolyamines are the polyoxypropylenediamines wherein X is a methyl radical; n is a number from 2 to 17, Z is a 1,2-propylene radical and r, is about 2 or 3.

According to another embodiment, the ureido terminated compounds contain polyether ureylene or thioureylene groups in the chain. In accordance with this aspect, a polyoxyalkylene ureylene or thioureylene having terminal primary amino groups is the oligomeric condensation product of a polyoxyalkylenepolyamine with a urea or thiourea forming compound. In accordance with this aspect of the invention, these ureido terminated polyether ureylene or thioureylene compounds are formed by initially reacting a molar excess of polyoxyalkylenepolyamine with a ureylene forming compound or a thioureylene forming compound to produce an oligomeric product having terminal primary amino groups. In a second step the primary amino terminated polyether product is reacted in a molar ratio of 1 mole of ureido forming compound for each mole of amine to form the ureido terminated compounds of the instant invention. The novel compounds formed in accordance this aspect of the invention can be depicted by the following formula

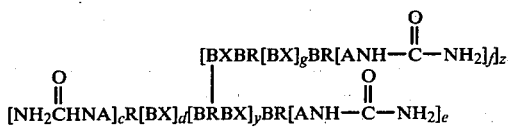

wherein A is a polyoxyalkylene radical containing from about 1 to 17 oxyalkylene groups, B is a polyoxyalkylene amino radical containing from about 1 to 17 oxyalkylene groups, R is a hydrocarbon radical having from 2 to 5 carbon atoms and forming from 2 to 4 oxycarbon linkages with A and B, X is a C=O radical, a C=S radical or a radical derived from a difunctional isocyanate having two

groups, c and d are from 1 to 3 chosen such that their sum is from 1 to 4, e is a number from 1 to 3, f is a number from 1 to 3, g is a number from 1 to 3, y is a number from 0 to about 5, and z is a number from 0 to 2.

The polyether ureylene or thioureylene precursors that may be reacted with urea to form terminal ureido containing compounds in accordance with this aspect of the instant invention can be depicted by the following formula:

wherein A is a polyoxyalkylene radical containing from about 1 to about 17 oxyalkylene groups wherein each oxyalkylene group contains from 2 to about 4 carbon atoms; B is a polyoxyalkylene amino radical containing from about 1 to 17 oxyalkylene groups wherein each oxyalkylene group contains from 2 to about 4 carbon atoms; R is a hydrocarbon radical having from 2 to 5 carbon atoms forming from 2 to 4 oxycarbon linkages with A and B; X is a C=O radical, a C=S radical or a radical derived from a difunctional isocyanate having two

groups; c and d are from 1 to 3 chosen such that their sum is 2 to 4; e is a number from 1 to 3; f is a number from 1 to 3; g is a number from 1 to 3; y is a number from 0 to about 5; z is a number from 0 to 2.

Preferably these precursors are depicted by the above formula wherein A corresponds to the formula:

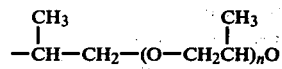

wherein n is a number from 0 to 16 and preferably a number from 1 to 10, B corresponds to the formula:

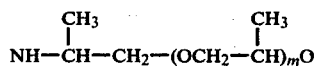

wherein m is a number from 0 to 16 and preferably a number from 1 to 10, c and d are from 1 to 2 chosen such that their sum is from 2 to 3, e is a number from 1 to 2, g is a number from 1 to 2, f is a number from 1 to 2, z is a number from 0 to 1, y is a number from 1 to 4, and X is a C=O radical.

The primary amino terminated polyether ureylene compound is preferably formed by reacting from about 2.0 mols to about 1.2 mols of the polyoxypropylenepolyamine with 1 mol of urea at temperatures from about 100° C. to about 200° C.

These polyether ureylenes can be formed by reaction of a polyoxyalkylenepolyamine wherein the alkylene contains from 2 to about 4 carbon atoms with urea, a ureylene forming compound, or an organic bifunctional isocyanate.

The primary amino terminated polyether thioureylene can be formed by reaction of a polyoxyalkylenepolyamine wherein the alkylene contains from 2 to about 4 carbon atoms with thiourea, a thioureylene forming compound or carbon disulfide.

The most preferred polyether thioureylene compound is that formed by reacting from about 5.0 mols to about 1.2 mols of polyoxypropylenepolyamine having a molecular weight of about 200 to about 2000 with 1 mol of carbon disulfide at temperatures from about 10° C. to about 150° C. It has been found that addition of greater than about 0.5 moles of carbon disulfide per mole of polyoxyalkylenepolyamine produces highly viscous reaction mixtures. Therefore, suitable nondeleterious diluents well known in the art may be utilized to facilitate the reaction when greater than 0.5 moles of carbon disulfide is used per mole of polyoxyalkylenepolyamine.

A preferred class of polyoxyalkylenepolyamines useful in forming the polyether compounds may be depicted by the formula:

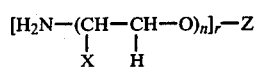

wherein X is hydrogen, a methyl radical or an ethyl radical; Z is a hydrocarbon radical having 2 to 5 carbon atoms forming from 2 to 4 external ether linkages; n is a number from 1 to about 17 and r is a number from 2 to 4. The most preferred polyoxyalkylenepolyamines are the polyoxypropylenediamines wherein X is a methyl radical, n is a number from 1 to 10, Z is a 1,2-propylene radical and r is about 2.

Whenever urea is employed as the reactant, the reaction proceeds with the evolution of ammonia. Since urea is bifunctional, each molecule of urea can react with two terminal amino groups of the polyoxyalkylenepolyamine. Consequently, it is possible to form polyureylenes in which the polyether ureylene unit repeats in the molecular structure.

While urea is the preferred reactant, other urea forming compounds may be utilized within the scope of the invention to supply the linking

radical. Since the polyoxyalkylenepolyamine reactant already contains terminal primary amino groups, compounds such as carbonyl diimidazole, phosgene, and diphenyl carbonate may be used to supply the

radical to form ureylene linkages without the liberation of ammonia.

Another class of polyether ureylenes which are useful are formed by reaction of polyoxyalkylenepolyamines with a bifunctional organic isocyanate obtained for instance from the phosgenated condensation product of aniline and formaldehyde. One suitable compound can be represented by the formula:

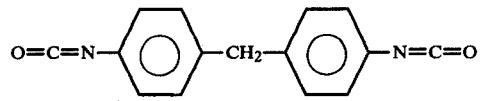

4,4'-diphenylmethanediisocyanate or the isomers thereof such as 2,4'-diphenylmethanediisocyanate. Mixtures of the isomers can also be used.

Whenever thiourea is employed as the reactant, the reaction proceeds with the evolution of ammonia. The functionality of the polyoxyalkylenepolyamine is dependent upon the number of terminal primary amino groups. Since thiourea, like urea, is bifunctional, each molecule of thiourea can react with two terminal amino groups of the polyoxyalkylenepolyamine. Consequently, it is possible to form polythioureylenes in which the thioureylene unit repeats in the molecular structure.

Whenever carbon disulfide is employed as the reactant in preparing the thiourea precursor compounds the reaction proceeds in two steps. The carbon disulfide is initially added to the reaction mixture at temperatures below the boiling point of carbon disulfide, e.g., less than 40° C. The reaction mixture is then heated to a temperature of from about 50° C. to about 150° C. until the evolution of hydrogen sulfide ceases. In this reaction one mole of carbon disulfide will react with two moles of the polyoxyalkylenediamine to form the polyether thioureylene product.

While carbon disulfide is the preferred reactant, other thioureylene forming compounds may be utilized within the scope of the invention to supply the linking

radical. Since the polyoxyalkylenepolyamine reactant already contains terminal primary amino groups, compounds such as a dithioisocyanate, and thiophosgene can be used to supply the

radical to form thioureylene linkages.

Another class of polyether containing compounds which are useful in the practice of this invention, are mixed polyether ureylene-thioureylene compounds. Thus in accordance with this aspect of the invention

radicals and

radicals are interspersed throughout the polyether chain to yield a mixed polyether ureylene-thioureylene.

The invention will be further illustrated by the following specific examples, which are given by way of illustration and not as limitations on the scope of this invention.

EXAMPLE I

In this example a polyether bisureide, in accordance with the instant invention, was prepared. Into a suitable reaction vessel, equipped with stirring apparatus, where added 36.5 lbs (40 moles) of a polyoxypropylenepolyamine having a molecular weight of approximately 400, and an analysis of 4.83 miliequivalents (meq.) primary amine/g (about 5.0 meq. total amine/g) sold under the tradename "JEFFAMINE ® D-400" by Jefferson Chemical Co., Austin, Texas 78751 and 15.89 lbs of urea (120 moles). The admixture, while being continuously stirred, was flushed with nitrogen and heated to 125° C. This temperature was maintained until the evolution of ammonia had diminished (approximately 120 minutes). The kettle temperature was then raised to about 130° C. and when ammonia development had again slowed, a second portion of 18.3 lbs (20 moles) of "JEFFAMINE ® D-400" was added slowly in aliquots over a 70 minute period while the temperature was maintained at between 130° C. and 133° C. While the temperature was maintained, the mixture was stirred for about 3½ hours until gas development had completely ceased. The crude reaction mixture was then stripped at 110° C./5 mm Hg to produce a resinous reaction product which analyzed as follows: 10.3% N, 0.02 meq. total amine/g.

EXAMPLE II

According to the procedure of Example I, 1980 grams (1 mole) of a polyoxypropylene polyamine having a molecular weight of about 2000 and analysis of 1.01 meq. primary amine/g sold under the tradename of "JEFFAMINE ® D-2000" was reacted with 180 grams (3.0 moles) urea by stirring the admixture under a nitrogen pad for 2 hours at 130°–134° C. A second portion of "JEFFAMINE ® D-2000" consisting of 990 grams (0.5 moles) was added over a 3 hour period at a temperature of about 132° C. The reaction mixture was maintained at 134° C. for another 70 minutes, during which time the admixture was vigorously stirred to continuously wash the sublimate on the upper surface of the reaction vessel. The crude reaction product was then stripped at 130° C./1.4 mm Hg to produce a viscous residue which upon analysis showed 2.54% N, 0.01 meq. total amine/g.

EXAMPLE III

Using the procedure and apparatus of Example I, a tris(ureide) was prepared by reacting and admixing 2169 grams (4.5 moles) of a 400 molecular weight triamine having an analysis of 6.23 meq. primary amine/gram and 810 grams (13.5 moles) urea at a temperature of about 134° C. After cessation of ammonia evolution, the crude reaction product was stripped at 140° C./1 mm/Hg to give a resinous product which upon analysis showed 13.57% N, 0.17 meq. total amine/g.

The following three examples (IV–VI) show the preparation of the polyether ureylene precursor having primary amine termination.

EXAMPLE IV

Into a reaction vessel were added 3,618 g (9.0 moles) of a polyoxypropylenepolyamine having a molecular weight of approximately 400 and an analysis of 4.98 meq. primary amine/g 5.0 meq. total amine/g. sold under the name "JEFFAMINE ® D-400" by Jefferson Chemical Co., Austin, Texas 78751, and 270 g of urea (4.5 moles). The mixture was heated gradually to 198° C. and maintained at this temperature until the evolution of ammonia ceased. The reaction mixture was then stripped at 130° C. at a pressure 1 mm Hg. A viscous liquid polyether ureylene having terminal primary amino groups was obtained having an osmometric molecular weight of 650 and which analyzed as follows: 6.6% N, 2.3 meq total amine/g., 2.20 meq. primary amine/g.

EXAMPLE V

According to the procedure of Example IV, 3,618 g (9.0 moles) of a polyoxypropylenepolyamine sold under the name "JEFFAMINE ® D-400" by Jefferson Chemical Co., Austin, Texas 78751 was reacted with 450 g of urea (7.5 moles). A viscous polyether ureylene having terminal primary amino groups was obtained having an osmometric molecular weight of approximately 1720 and which analyzed as follows: 6.19% N, 0.91 meq. total amine/g, 0.71 meq. primary amine/g.

EXAMPLE VI

In a reaction vessel under an inert atmosphere, 402 g (1.0 mol) of a polyoxypropylenepolyamine sold under the name "JEFFAMINE ® D-400" by Jefferson Chemical Co., Austin, Texas 78751 was heated to 170° C. with vigorous stirring. The heat source was then removed and 66 g (0.5 meq) of a polyisocyanate obtained by phosgenation of an aniline-formaldehyde condensate (7.56 meq. NCO/g) was added to the amine over a period of 5 minutes. The reaction mixture was then heated to 245°–250° C. and maintained at that temperature for 15 minutes. The reaction mixture was then cooled. The polyether ureylene having terminal primary amino groups was found to have an osmometric molecular weight of 560 and analyzed as follows: 7.35% N, 2.71 meq. primary amine/g.

The following two examples (VII–VIII) show preparation of the polyether thioureylene precursor and the polyether ureylene-thioureylene precursor, respectively.

EXAMPLE VII

Into a reaction vessel containing 824 g (1.89 mol) of a polyoxypropylenediamine having a molecular weight of approximately 436 was added 23 ml (0.38 mol) of carbon disulfide at a temperature of 10° C. The carbon disulfide was added below the surface of the liquid in the reaction vessel over a period of 70 minutes. Over the next hour, the contents of the reaction vessel were warmed to 25° C. and then the mixture was heated at 100° C. for 30 minutes until the evolution of hydrogen sulfide ceased. The reaction mixture was then stripped at 100° C. at a pressure of 1 mm Hg. The polyether thioureylene obtained had an osmometric molecular weight of 522 and analyzed as follows: 0.67% N, 3.38 meq primary amine/g.

EXAMPLE VIII

A mixed polyether ureylene-thioureylene compound was prepared in three steps. First, a polyether ureylene having terminal primary amino groups was prepared by reaction 2,916 (12.0 moles, 8.23 meq. primary amine/g) of a polyoxypropylenepolyamine having a molecular weight of about 240 sold by Jefferson Chemical Company, Austin, Texas 78751 under the name "JEFFAMINE ® D-230" with 360 g (6.0 moles) of urea at a temperature of 198° C. until the evolution of ammonia has ceased.

In a second step, 702 g (about 1.5 moles) of the polyether ureylene prepared in the first step was brought to a temperature of about 20° C. and 46 ml (0.75 moles) of carbon disulfide was added over a period of 65 minutes. At the end of the carbon disulfide addition, the temperature of the reaction mixture had increased to about 95° C. The reaction mixture was then heated to a temperature of about 100° C. where it was maintained for about 100 minutes.

In the final step, the reaction mixture obtained in step 2 was stripped in a rotary evaporator at 0.7 mm Hg (bath temperature 100° C.) to yield a mixed polyether ureylenethioureylene compound having terminal primary amino groups. The mixed compound showed an osmometric molecular weight of 930 and analyzed as follows: 1.99 meq primary amine/g.

EXAMPLE IX

In this example, a urea-formaldehyde cured resin was prepared using the polyoxypropylene bis(ureide) obtained in Example I. In an appropriate vessel 516 g of the resinous reaction product obtained in the Example I was heated at 50° to 60° C. To the heated resin was added 266.4 g of 37% aqueous formaldehyde solution with stirring. A clear colorless solution resulted which on analysis showed: Brookfield viscosity, 1400 cp at 25° C.; pH, 8.3; 1.04% free formaldehyde.

The product was stored for about 4 weeks at room temperature and again analyzed. The stored product showed: Brookfield viscosity, 2200 cp at 25° C.; pH, 7.6; 0.63% free formaldehyde.

The formaldehyde urea adduct thus prepared was then cured with ammonium chloride. Into a standard aluminum mold was poured a mixture of 97 g of the adduct and 1 g ammonium chloride dissolved in 3.1 g water. The mold was cured at 80°–90° C. for one hour. A resilient, dense material was obtained which showed minimal shrinkage after being stored for extended times.

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A polyether polyureide comprising a ureido-terminated polyoxyalkylene selected from the group consisting of a compound of the formula:

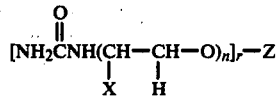

wherein X is hydrogen, a methyl radical or an ethyl radical; Z is a hydrocarbon radical having 2 to 5 carbon atoms forming from 2 to 4 external ether linkages; n is a number from 1 to about 20; and, r is a number from 2 to 4; and a compound of the formula:

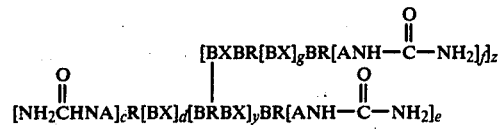

wherein A is a polyoxyalkylene radical containing from about 1 to 17 oxyalkylene groups, B is a polyoxyalkylene amino radical containing from about 1 to 17 oxyalkylene groups, R is a hydrocarbon radical having from 2 to 5 carbon atoms and forming from 2 to 4 oxycarbon linkages with A and B, X is a C=O radical, a C=S radical or a radical derived from a difunctional isocyanate having two

groups, c and d are from 1 to 3 chosen such that their sum is from 1 to 4, e is a number from 1 to 3, f is a number from 1 to 3, g is a number from 1 to 3, y is a number from 0 to about 5, and z is a number from 0 to 2.

2. The polyether polyureide of claim 1 wherein X is a methyl radical; n is a number from 2 to 17, Z is a 1,2-propylene radical and r is about 2 or 3.

3. The polyether polyureide of claim 1 wherein A corresponds to the formula:

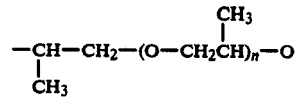

wherein n is a number from 0 to 15; B corresponds to the formula:

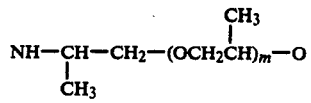

wherein m is a number from 0 to 15; c and d are from 1 to 2 and chosen so that their sum is from 2 to 3; e is a number from 1 to 2; g is a number from 1 to 2; f is a number from 1 to 2; z is a number from 0 to 1; y is a number from 1 to 4; and X is a C=O radical.

4. The polyether polyureide of claim 3 wherein n and m are, independently, numbers from about 1 to 10.

5. The polyether polyureide of claim 1 wherein X is the radical selected from a group consisting of

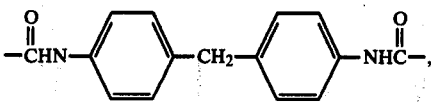

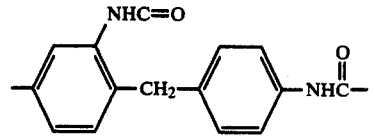

and mixtures thereof.

6. A polyether polyureide comprises a ureido-terminated polyoxyalkylene material, formed by the reaction of a ureido group forming compound with a compound selected from a polyoxyalkylenepolyamine of the formula

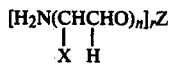

wherein X is a hydrogen, a methyl radical or an ethyl radical; Z is a hydrocarbon radical having from 2 to 5 carbon atoms forming from 2 to 4 external ether linkages; n is a number from 1 to about 20 and r is a number from 2 to 4 and a polyoxyalkylene ureylene or thioureylene having terminal primary amino groups of the formula

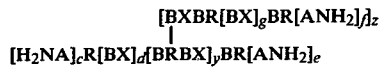

wherein A is a polyoxyalkylene radical containing from about 1 to about 17 oxyalkylene groups wherein each oxyalkylene group contains from 2 to about 4 carbon atoms; B is a polyoxyalkylene amino radical containing from about 1 to 17 oxyalkylene groups wherein each oxyalkylene group contains from 2 to about 4 carbon atoms; R is a hydrocarbon radical having from 2 to 5 carbon atoms forming from 2 to 4 oxycarbon linkages with A and B; X is a C=O radical, a C=S radical or a radical derived from a difunctional isocyanate having two —NHC— groups; c and d are from 1 to 3 chosen such that their sum is 2 to 4; e is a number from 1 to 3; f is a number from 1 to 3; g is a number from 1 to 3; y is a number from 0 to about 5; z is a number from 0 to 2 in a ratio of about 1 mole of ureide forming compound for each terminal primary amine group at temperatures in the range of from about 120° C. to about 150° C.

7. The polyether polyureide of claim 6 wherein said ureido group forming compound is selected from urea and isocyanates of the general formula $M^+NCO^-$ wherein $M^+$ is an alkali metal.

8. The polyether polyureide of claim 7 wherein X is a methyl radical, n is a number from 2 to 17, Z is a 1,2-propylene radical and r is about 2 or 3.

9. The polyether polyureide of claim 7 wherein A corresponds to the formula:

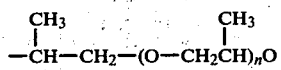

wherein n is a number from 0 to 16 and preferably a number from 1 to 10, B corresponds to the formula:

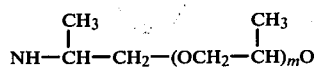

wherein m is a number from 0 to 16 and preferably a number from 1 to 10, c and d are from 1 to 2 chosen such that their sum is from 2 to 3, e is a number from 1 to 2, g is a number from 1 to 2, f is a number from 1 to 2, z is a number from 0 to 1, y is a number from 1 to 4, and X is a C=O or C=S radical.

10. The polyether polyureide of claim 9 wherein X is the radical selected from a group consisting of

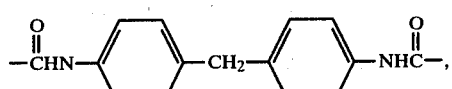

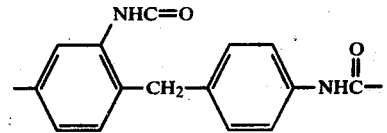

and mixtures thereof.

11. The polyether polyureide of claim 9 wherein X is a mixture of C=O and C=S radicals throughout the formula such as to yield a mixed polyether ureylenethioureylene.

12. A polyether polyureide comprising a ureidoterminated polyoxyalkylene of the formula:

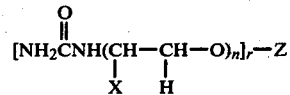

wherein X is hydrogen, a methyl radical or an ethyl radical; Z is a hydrocarbon radical having 2 to 5 carbon atoms forming from 2 to 4 external ether linkages; n is a number from 1 to about 20; and, r is a number from 2 to 4.

13. The polyether polyureide of claim 12 wherein X is a methyl radical; n is a number from 2 to 17, Z is a 1,2-propylene radical and r, is about 2 or 3.

14. The polyether polyureide of claim 13 wherein r is 2 and the ureido terminated polyoxyalkylene has a molecular weight of about 2000.

15. The polyether polyureide of claim 13 wherein the ureido terminated polyoxyalkylene has a molecular weight of about 400.

16. A polyether polyureide formed by the reaction of a ureido group forming compound with a compound selected from a polyoxyalkylenepolyamine of the formula

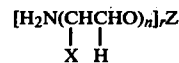

wherein X is a hydrogen, a methyl radical or an ethyl radical; Z is a hydrocarbon radical having from 2 to 5 carbon atoms forming from 2 to 4 external ether linkages; n is a number from 1 to about 20 and r is a number from 2 to 4 wherein the ratio of said ureido group forming compound is one mole to each terminal primary amino group at temperatures in the range of about 120° C. to about 150° C.

17. The polyether polyureide of claim 16 wherein the ureido forming compound is selected from urea and isocyanates of the general formula $M^+NCO^-$ wherein $M^+$ is an alkali metal.

18. The polyether polyureide of claim 17 wherein the ureido forming compound is urea and wherein X is a methyl radical, n is a number from 2 to 17, Z is a 1,2-propylene radical and r is about 2 or 3.

19. The polyether polyureide of claim 18 wherein r is 2 and said polyoxyalkylenepolyamine has a molecular weight of about 2000.

20. The polyether polyureide of claim 18 wherein said polyoxyalkylenepolyamine has a molecular weight of about 400.

21. A method for producing a polyether polyureide comprising the step of:

reacting a ureido group forming compound with a compound selected from a polyoxyalkylenepolyamine of the formula

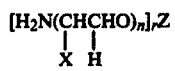

wherein X is a hydrogen, a methyl radical or an ethyl radical; Z is a hydrocarbon radical having from 2 to 5 carbon atoms forming from 2 to 4 external ether linkages; n is a number from 1 to about 20 and r is a number from 2 to 4 in a ratio of 1 mole of ureido group forming compound to each terminal amine group at temperatures in the range of 120° C. to 150° C.

22. The method of claim 21 wherein the ureido forming compound is selected from urea and isocyanates of the general formula M+NCO− wherein M+ is an alkali metal.

23. The method of claim 21 wherein the ureido forming compound is urea and wherein X is a methyl radical, n is a number from 2 to 17, Z is a 1,2-propylene radical and r is about 2 or 3.

24. The method of claim 23 wherein r is 2 and said polyoxyalkylenepolyamine has a molecular weight of about 2000.

25. The method of claim 23 wherein said polyoxyalkylenepolyamine has a molecular weight of about 400.

* * * * *